US012581236B2

(12) United States Patent
Shimauchi et al.

(10) Patent No.: US 12,581,236 B2
(45) Date of Patent: Mar. 17, 2026

(54) ELECTRONIC STETHOSCOPE SIGNAL PROCESSOR, ELECTRONIC STETHOSCOPE SYSTEM, ELECTRONIC STETHOSCOPE SIGNAL PROCESSING PROGRAM AND ELECTRONIC STETHOSCOPE SIGNAL PROCESSING METHOD

(71) Applicants: Nisshinbo Micro Devices Inc., Tokyo (JP); Kanazawa Institute of Technology, Ishikawa (JP)

(72) Inventors: Suehiro Shimauchi, Ishikawa (JP); Kanako Takemoto, Saitama (JP); Masashi Kitagawa, Saitama (JP); Chunhui Pan, Saitama (JP); Daisuke Sakata, Saitama (JP); Tei Yui, Saitama (JP); Hajime Fujiwara, Saitama (JP)

(73) Assignee: Nisshinbo Micro Devices Inc., Tokyo (JP)

( * ) Notice: Subject to any disclaimer, the term of this patent is extended or adjusted under 35 U.S.C. 154(b) by 178 days.

(21) Appl. No.: 18/407,904

(22) Filed: Jan. 9, 2024

(65) Prior Publication Data

US 2024/0259729 A1     Aug. 1, 2024

Related U.S. Application Data

(60) Provisional application No. 63/441,585, filed on Jan. 27, 2023.

(51) Int. Cl.
H04R 3/00 (2006.01)
A61B 7/04 (2006.01)
(Continued)

(52) U.S. Cl.
CPC ................ H04R 3/04 (2013.01); A61B 7/04 (2013.01); H04R 1/46 (2013.01); H04R 3/005 (2013.01)

(58) Field of Classification Search
CPC ...... A61B 7/04; H04R 1/46; G10K 11/17854; G10K 11/17879; G10L 21/0208
See application file for complete search history.

(56) References Cited

U.S. PATENT DOCUMENTS

2015/0119758 A1*  4/2015  Rogers ................. A61B 5/7203
                                                    600/586
2016/0045183 A1*  2/2016  Lee ...................... A61B 8/5223
                                                    600/443
2022/0005491 A1*  1/2022  Mo ..................... G10L 21/0216

OTHER PUBLICATIONS

D1: Samir B. Patel, Thomas F. Callahan, Matthew G. Callahan, James T. Jones, George P. Graber, Kirk S. Foster, Kenneth Glifort, and George R. Wodicka, "An adaptive noise reduction stethoscope for auscultation in high noise environments", The Journal of the Acoustical Society of America, vol. 103, No. 5, pp. 2483-2491, 1998.

* cited by examiner

*Primary Examiner* — James K Mooney
(74) *Attorney, Agent, or Firm* — Ohlandt, Greeley and Perle, LLP.

(57) ABSTRACT

Extract intracorporeal sounds (such as low-frequency-range heart sounds or breath sounds) by not only reducing steady noise (such as low-frequency-range environmental sounds or noise) but also reducing unexpected noise (such as high-frequency-range cries or speaking voices). This keeps up the intracorporeal sounds (such as low-frequency-range heart sounds or breath sounds), while reducing the unexpected noise (such as high-frequency-range cries or speaking voices), using an improved adaptive filter unit and an improved nonlinear filter unit. Here, a reduction level of the unexpected noise (such as high-frequency-range cries or speaking voices) and a level of keeping up the intracorporeal sounds (such as low-frequency-range heart sounds or breath sounds) are quantitatively calculated.

12 Claims, 9 Drawing Sheets

[1]

(51) Int. Cl.
     *H04R 1/46*             (2006.01)
     *H04R 3/04*             (2006.01)

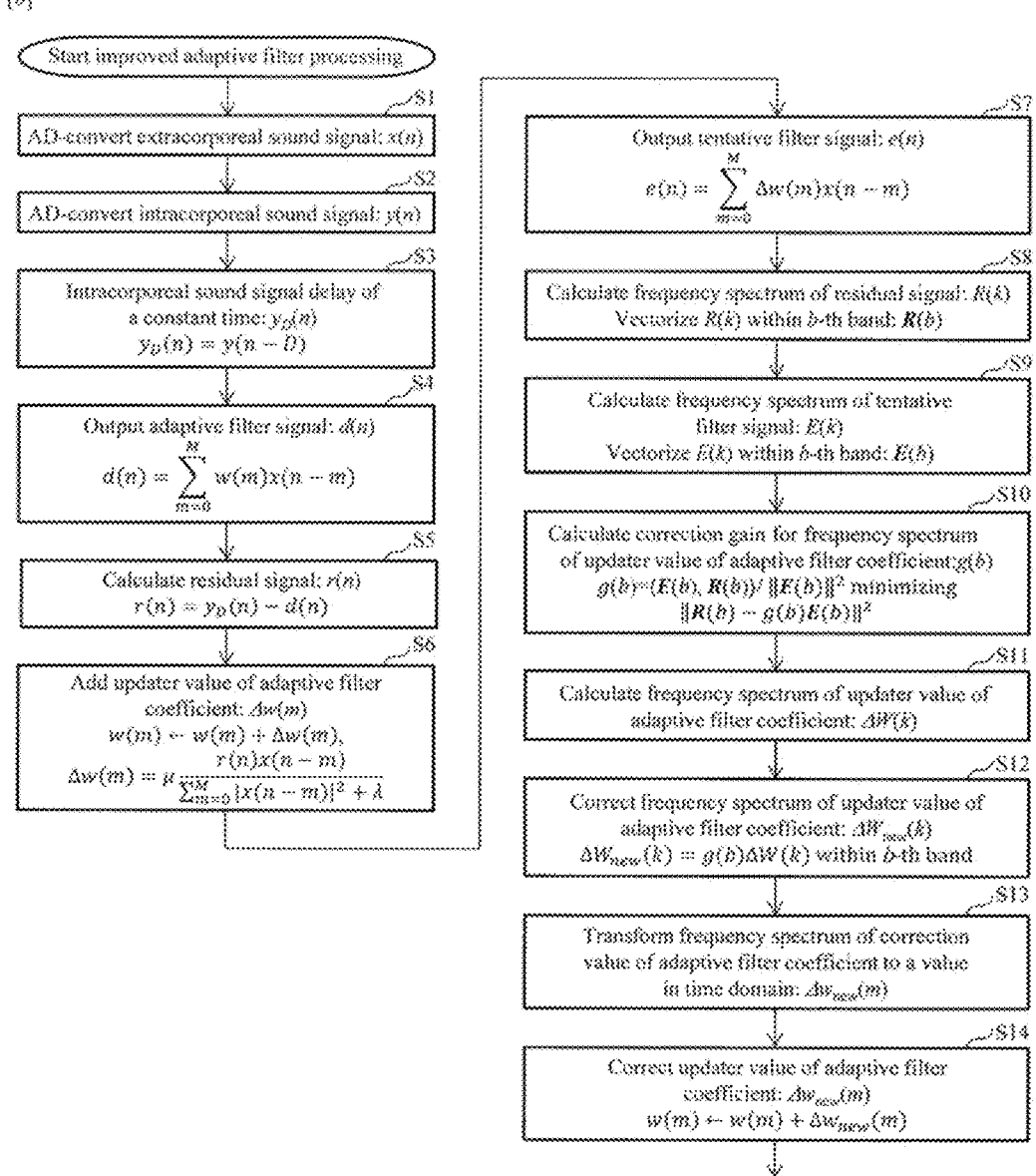

Start improved adaptive filter processing

S1
AD-convert extracorporeal sound signal: $x(n)$

S2
AD-convert intracorporeal sound signal: $y(n)$

S3
Intracorporeal sound signal delay of
a constant time: $y_D(n)$
$$y_D(n) = y(n - D)$$

S4
Output adaptive filter signal: $d(n)$
$$d(n) = \sum_{m=0}^{M} w(m)x(n - m)$$

S5
Calculate residual signal: $r(n)$
$$r(n) = y_D(n) - d(n)$$

S6
Add updater value of adaptive filter
coefficient: $\Delta w(m)$
$$w(m) \leftarrow w(m) + \Delta w(m),$$
$$\Delta w(m) = \mu \frac{r(n)x(n - m)}{\sum_{m=0}^{M} |x(n - m)|^2 + \lambda}$$

S7
Output tentative filter signal: $e(n)$
$$e(n) = \sum_{m=0}^{M} \Delta w(m)x(n - m)$$

S8
Calculate frequency spectrum of residual signal: $R(k)$
Vectorize $R(k)$ within $b$-th band: $R(b)$ S9
Calculate frequency spectrum of tentative
filter signal: $E(k)$
Vectorize $E(k)$ within $b$-th band: $E(b)$ S10
Calculate correction gain for frequency spectrum
of updater value of adaptive filter coefficient: $g(b)$
$g(b)=(E(b), R(b))/ \|E(b)\|^2$ minimizing
$\|R(b) - g(b)E(b)\|^2$ S11
Calculate frequency spectrum of updater value of
adaptive filter coefficient: $\Delta W(k)$ S12
Correct frequency spectrum of updater value of
adaptive filter coefficient: $\Delta W_{new}(k)$
$\Delta W_{new}(k) = g(b)\Delta W(k)$ within $b$-th band S13
Transform frequency spectrum of correction
value of adaptive filter coefficient to a value
in time domain: $\Delta w_{new}(m)$ S14
Correct updater value of adaptive filter
coefficient: $\Delta w_{new}(m)$
$$w(m) \leftarrow w(m) + \Delta w_{new}(m)$$

End improved adaptive filter processing

ELECTRONIC STETHOSCOPE SIGNAL PROCESSOR, ELECTRONIC STETHOSCOPE SYSTEM, ELECTRONIC STETHOSCOPE SIGNAL PROCESSING PROGRAM AND ELECTRONIC STETHOSCOPE SIGNAL PROCESSING METHOD

CROSS-REFERENCED APPLICATION

This application claim priority to U.S. Provisional Application Ser. No. 63/441,585, filed on Jan. 27, 2023, which is incorporated herein in its' entirety by reference thereto.

BACKGROUND

Field of the Invention

The present disclosure relates to an electronic stethoscope that reduces extracorporeal sounds and extracts intracorporeal sounds.

Description of the Related Art

An electronic stethoscope that reduces extracorporeal sounds and extracts intracorporeal sounds is disclosed in Non-patent Literature 1 etc. Here, an extracorporeal sound collector of the electronic stethoscope collects extracorporeal sounds and outputs an extracorporeal sound signal. Meanwhile, an intracorporeal sound collector of the electronic stethoscope collects intracorporeal sounds and outputs an intracorporeal sound signal. However, the intracorporeal sound signal includes a diffracted element of the extracorporeal sounds from an outside of the electronic stethoscope to the intracorporeal sound collector.

Then, an adaptive filter unit of a signal processor has adaptive filter coefficients simulating a diffraction property of the extracorporeal sounds from the outside of the electronic stethoscope to the intracorporeal sound collector, receives the extracorporeal sound signal obtained from the extracorporeal sound collector, and outputs an adaptive filter signal. Furthermore, a residual signal calculator of the signal processor subtracts the adaptive filter signal from the intracorporeal sound signal, obtained from the intracorporeal sound collector, to calculate a residual signal obtained by taking the diffracted element of the extracorporeal sound signal from the intracorporeal sound signal.

Non-patent Literature 1: Samir B. Patel, Thomas F. Callahan, Matthew G. Callahan, James T. Jones, George P. Graber, Kirk S. Foster, Kenneth Glifort, and George R. Wodicka, "An adaptive noise reduction stethoscope for auscultation in high noise environments", The Journal of the Acoustical Society of America, vol. 103, no. 5, pp. 2483-2491, 1998.

SUMMARY

Here, the adaptive filter unit and the residual signal calculator of the signal processor can reduce steady noise (such as low-frequency-range environmental sounds or noise) and extract intracorporeal sounds (such as low-frequency-range heart sounds or breath sounds). However, the adaptive filter unit and the residual signal calculator of the signal processor cannot reduce unexpected noise (such as high-frequency-range cries or speaking voices) sufficiently or extract the intracorporeal sounds (such as low-frequency-range heart sounds or breath sounds). Their reasons will be described later using FIG. 2 to FIG. 4.

Therefore, in order to solve the problem, it is an object of the present disclosure to extract intracorporeal sounds (such as low-frequency-range heart sounds or breath sounds) by not only reducing steady noise (such as low-frequency-range environmental sounds or noise) but also reducing unexpected noise (such as high-frequency-range cries or speaking voices).

In order to solve the problem, in an adaptive filter, a tentative filter unit has tentative filter coefficients chosen to be equal to updater values of the adaptive filter coefficients, receives an extracorporeal sound signal, and outputs a tentative filter signal. Then, a correction gain calculator calculates correction gains for a frequency spectrum of the updater values of the adaptive filter coefficients as relatively large values within high frequency bands, dominated with cries or speaking voices, where a frequency-band-limited correlation between a frequency spectrum of a residual signal and a frequency spectrum of the tentative filter signal is high. In contrast, the correction gain calculator calculates the correction gains, as a relatively small values, within low frequency bands, dominated with heart or breath sounds, where the frequency-band-limited correlation between the frequency spectrum of the residual signal and the frequency spectrum of the tentative filter signal is low.

Specifically, the present disclosure is an electronic stethoscope signal processor including: an adaptive filter unit that has adaptive filter coefficients simulating a diffraction property of an extracorporeal sound from an outside of an electronic stethoscope to an intracorporeal sound collector, receives an extracorporeal sound signal obtained from an extracorporeal sound collector, and outputs an adaptive filter signal; a residual signal calculator that subtracts the adaptive filter signal from an intracorporeal sound signal, obtained from the intracorporeal sound collector, to calculate a residual signal intended to be a result of taking a diffracted component of the extracorporeal sound signal from the intracorporeal sound signal; a filter coefficient updater that adds updater values of the adaptive filter coefficients to current values of the adaptive filter coefficients so as to lower a correlation in a time axis direction between the adaptive filter signal and the residual signal; a tentative filter unit that has tentative filter coefficients chosen to be equal to the updater values of the adaptive filter coefficients, receives the extracorporeal sound signal, and outputs a tentative filter signal; a correction gain calculator that calculates correction gains for a frequency spectrum of the updater values of the adaptive filter coefficients, as relatively large values, within high frequency bands where a frequency-band-limited correlation between a frequency spectrum of the residual signal and a frequency spectrum of the tentative filter signal is high, and calculates the correction gains for the frequency spectrum of the updater values of the adaptive filter coefficients, as relatively small values, within low frequency bands where the frequency-band-limited correlation between the frequency spectrum of the residual signal and the frequency spectrum of the tentative filter signal is low; and a filter coefficient correction unit that calculates a correction value, relative to the updater values of the adaptive filter coefficients, based on the correction gains for the frequency spectrum of the updater values of the adaptive filter coefficients.

This structure allows for keeping up intracorporeal sounds (such as low-frequency-range heart sounds or breath sounds), while reducing unexpected noise (such as high-frequency-range cries or speaking voices), using an adaptive filter.

The present disclosure is the electronic stethoscope signal processor in which the correction gain calculator calculates the correction gains for the frequency spectrum of the updater values of the adaptive filter coefficients, corresponding to each band such that, based on a frequency-band-limited correlation between the frequency spectrum of the residual signal and the frequency spectrum of the tentative filter signal resulting from multiplication by the correction gains, corresponding to each band, a spectral-shape error between the residual signal and the tentative filter signal resulting from multiplication by the correction gains is minimized.

This structure allows for quantitatively calculating a reduction level of the unexpected noise (such as high-frequency-range cries or speaking voices) and a level of keeping up the intracorporeal sounds (such as low-frequency-range heart sounds or breath sounds).

The present disclosure is the electronic stethoscope signal processor further including: a filter reduction amount calculator that calculates a reduction amount of the frequency spectrum of the residual signal, relative to a frequency spectrum of the intracorporeal sound signal, to calculate a reduction amount by the adaptive filter unit; and a residual signal reduction unit that largely reduces the frequency spectrum of the residual signal within frequency bands where the reduction amount by the adaptive filter unit is large, and retains or sparingly reduces the frequency spectrum of the residual signal within frequency bands where the reduction amount by the adaptive filter unit is small.

This structure allows for keeping up the intracorporeal sounds (such as low-frequency-range heart sounds or breath sounds), while reducing the unexpected noise (such as high-frequency-range cries or speaking voices), using a nonlinear filter.

In order to solve the problem, in the nonlinear filter, the filter reduction amount calculator calculates a reduction amount of the frequency spectrum of the residual signal, relative to the frequency spectrum of the intracorporeal sound signal, to calculate a reduction amount by the adaptive filter unit. Then, the residual signal reduction unit largely reduces the frequency spectrum of the residual signal within frequency bands where the reduction amount by the adaptive filter unit is large (such as high-frequency-range cries or speaking voices). In contrast, the residual signal reduction unit retains the frequency spectrum of the residual signal within frequency bands where the reduction amount by the adaptive filter unit is small (such as low-frequency-range heart sounds or breath sounds).

Specifically, the present disclosure is an electronic stethoscope signal processor including: an adaptive filter unit that has adaptive filter coefficients simulating a diffraction property of an extracorporeal sound from an outside of an electronic stethoscope to an intracorporeal sound collector, receives an extracorporeal sound signal obtained from an extracorporeal sound collector, and outputs an adaptive filter signal; a residual signal calculator that subtracts the adaptive filter signal from an intracorporeal sound signal, obtained from the intracorporeal sound collector, to calculate a residual signal intended to be a result of taking a diffracted component of the extracorporeal sound signal from the intracorporeal sound signal; a filter coefficient updater that adds updater values of the adaptive filter coefficients to current values of the adaptive filter coefficients so as to lower a correlation in a time axis direction between the adaptive filter signal and the residual signal; a filter reduction amount calculator that calculates a reduction amount of a frequency spectrum of the residual signal, relative to a frequency spectrum of the intracorporeal sound signal, to calculate a reduction amount by the adaptive filter unit; and a residual signal reduction unit that largely reduces the frequency spectrum of the residual signal within frequency bands where the reduction amount by the adaptive filter unit is large, and retains or sparingly reduces the frequency spectrum of the residual signal within frequency bands where the reduction amount by the adaptive filter unit is small.

This structure allows for keeping up the intracorporeal sounds (such as low-frequency-range heart sounds or breath sounds), while reducing the unexpected noise (such as high-frequency-range cries or speaking voices), using a nonlinear filter.

The present disclosure is the electronic stethoscope signal processor further including a residual signal local minimum smoothing unit that calculates a local minimum smoothing spectrum of the residual signal so as to retain a local minimal value of the frequency spectrum of the residual signal. The residual signal reduction unit largely reduces the frequency spectrum of the residual signal to a spectrum further approaching the local minimum smoothing spectrum of the residual signal, within the frequency bands the reduction amount by the adaptive filter unit is large, and retains the frequency spectrum of the residual signal or sparingly reduces the frequency spectrum of the residual signal to a spectrum approaching the local minimum smoothing spectrum of the residual signal, within the frequency bands where the reduction amount by the adaptive filter unit is small.

This structure allows for quantitatively calculating the reduction level of the unexpected noise (such as high-frequency-range cries or speaking voices) and the level of keeping up the intracorporeal sounds (such as low-frequency-range heart sounds or breath sounds).

The present disclosure is an electronic stethoscope system including: the above-described electronic stethoscope signal processor; the extracorporeal sound collector that collects an extracorporeal sound and outputs the extracorporeal sound signal; and the intracorporeal sound collector that collects an intracorporeal sound and outputs the intracorporeal sound signal.

This structure allows for extracting the intracorporeal sounds (such as low-frequency-range heart sounds or breath sounds) by reducing the unexpected noise (such as high-frequency-range cries or speaking voices).

The present disclosure is an electronic stethoscope signal processing program for instructing a computer to execute each processing step by each component unit of the above-described electronic stethoscope signal processor.

This structure allows for extracting the intracorporeal sounds (such as low-frequency-range heart sounds or breath sounds) by reducing the unexpected noise (such as high-frequency-range cries or speaking voices).

The present disclosure is an electronic stethoscope signal processing method including each processing step by each component unit of the electronic stethoscope signal processor described above.

This structure allows for extracting the intracorporeal sounds (such as low-frequency-range heart sounds or breath sounds) by reducing the unexpected noise (such as high-frequency-range cries or speaking voices).

Thus, the present disclosure allows for extracting intracorporeal sounds (such as low-frequency-range heart sounds or breath sounds) by not only reducing steady noise (such as low-frequency-range environmental sounds or noise) but also reducing unexpected noise (such as high-frequency-range cries or speaking voices).

BRIEF DESCRIPTION OF THE DRAWINGS

FIG. 6 is a diagram illustrating a processing procedure of the improved adaptive filter unit of the present disclosure.

DESCRIPTION OF THE EMBODIMENTS

Embodiments of the present disclosure will be described by referring to the accompanying drawings. The embodiments described below are examples of implementation of the present disclosure, and the present disclosure is not limited to the following embodiments.
(Problem Solved by Electronic Stethoscope System of Present Disclosure)

Figure 1:
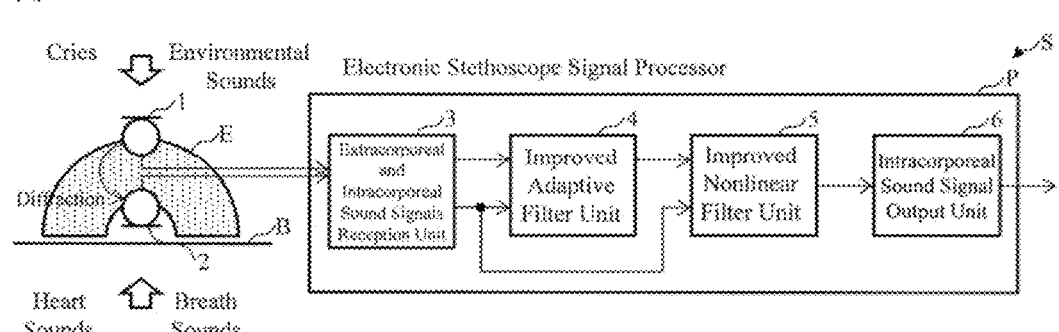
FIG. 1 is a diagram illustrating components of an electronic stethoscope system of the present disclosure.

FIG. 1 illustrates components of an electronic stethoscope system of the present disclosure. An electronic stethoscope system S includes an electronic stethoscope E and an electronic stethoscope signal processor P. The electronic stethoscope E includes an extracorporeal sound collector 1 and an intracorporeal sound collector 2. The electronic stethoscope signal processor P includes an extracorporeal and intracorporeal sound signals reception unit 3, an improved adaptive filter unit 4, an improved nonlinear filter unit 5 and an intracorporeal sound signal output unit 6, and is achievable by installing an electronic stethoscope signal processing program illustrated in FIG. 6 and FIG. 9 on a computer.

The electronic stethoscope E is a sensor device for collecting intracorporeal sounds via a body surface B and obtaining an intracorporeal sound signal. The extracorporeal sound collector 1 collects extracorporeal sounds and outputs an extracorporeal sound signal. The intracorporeal sound collector 2 collects intracorporeal sounds and outputs an intracorporeal sound signal. Examples of the extracorporeal sounds include low-frequency-range environmental sounds or noise, high-frequency-range cries or speaking voices, and the like. Examples of the intracorporeal sounds include low-frequency-range heart sounds or breath sounds, and the like. However, the intracorporeal sound signal includes a diffracted component of the extracorporeal sounds from an outside of the electronic stethoscope E to the intracorporeal sound collector 2.

Figure 2:
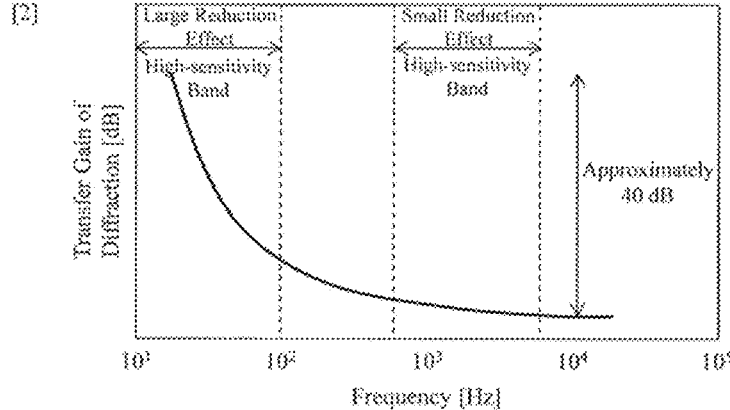
FIG. 2 is a diagram illustrating a problem solved by the electronic stethoscope system of the present disclosure.
Figure 3:
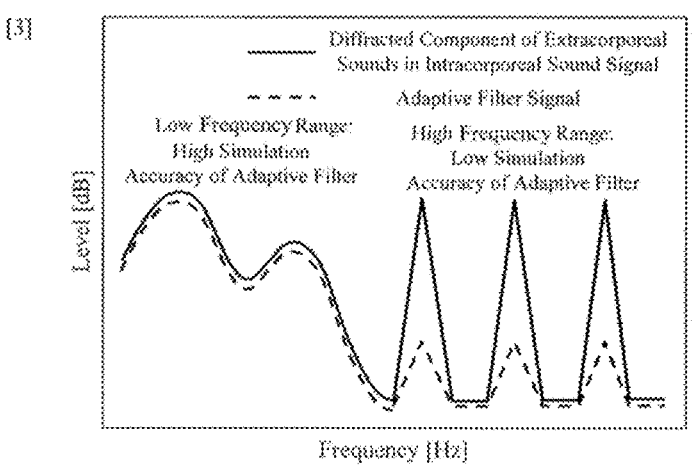
FIG. 3 is a diagram illustrating a problem solved by the electronic stethoscope system of the present disclosure.
Figure 4:
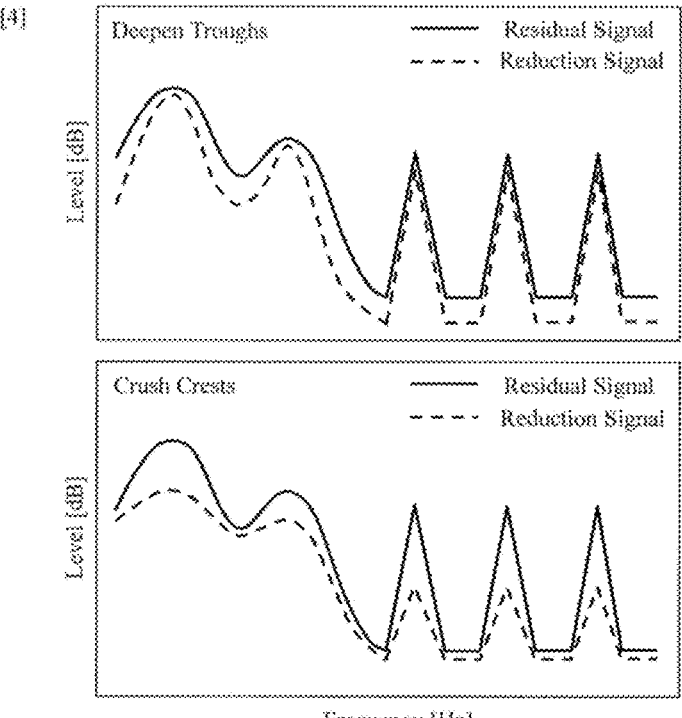
FIG. 4 is a diagram illustrating a problem solved by the electronic stethoscope system of the present disclosure.

FIG. 2 to FIG. 4 illustrate problems solved by the electronic stethoscope system of the present disclosure. In FIG. 2, a relative transfer gain of diffraction of the extracorporeal sounds from the outside of the electronic stethoscope E to the intracorporeal sound collector 2 is large in a low frequency range and small in a high frequency range (for example, a difference of approximately 40 dB). Accordingly, a reduction effect by an adaptive filter of the related art is large in a low frequency range and small in a high frequency range. On the other hand, an equal-loudness contour (a contour line of sounds that are perceived as equally loud by human ears) has a high-sensitivity band of the order of several hundreds of Hz to several thousands of Hz in addition to a high-sensitivity band of the order of several tens of Hz to 100 Hz. Accordingly, as long as the reduction effect by the adaptive filter of the related art is not enough in a high frequency range, in spite of a small relative transfer gain of diffraction of the extracorporeal sounds from the outside of the electronic stethoscope E to the intracorporeal sound collector 2 in the high frequency range, the extracorporeal sounds in the high frequency range are still loudly heard by human ears and prevent the human ears from hearing low-frequency-range intracorporeal sounds.

Figure 7:
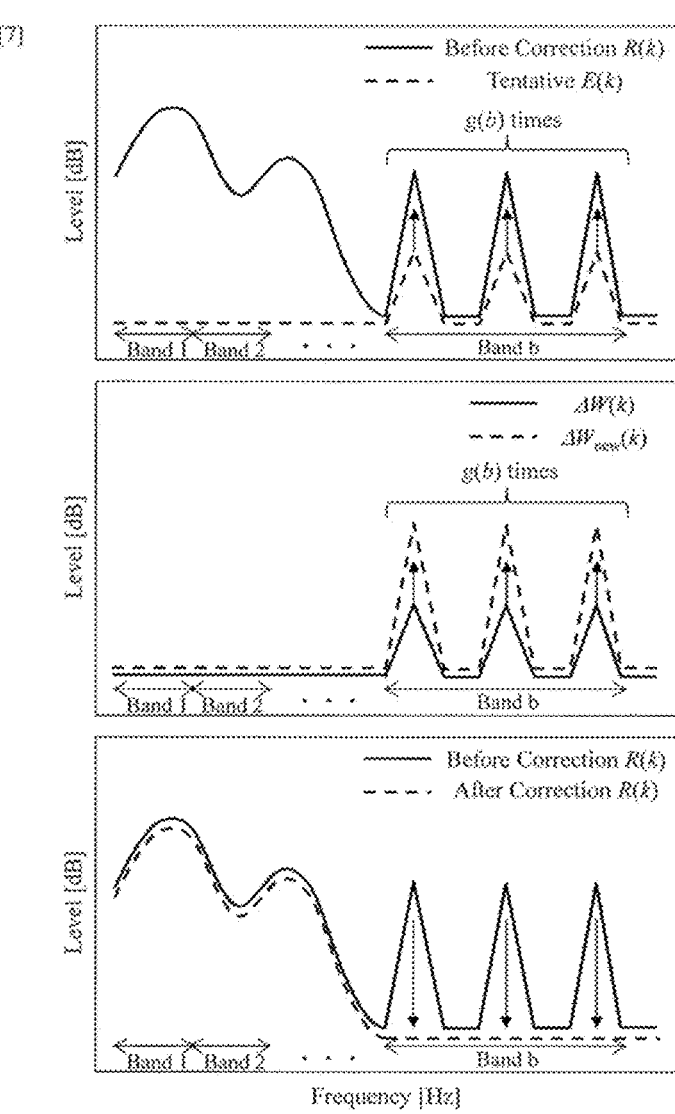
FIG. 7 is a diagram illustrating a processing concept of the improved adaptive filter unit of the present disclosure.

FIG. 3 is a schematic diagram of an output signal of a conventional adaptive filter. In a low frequency range where a transfer gain of diffraction of extracorporeal sounds is high, a coefficient of the adaptive filter is easy to update, and simulation accuracy of a diffracted component of extracorporeal sounds in an intracorporeal sound signal is high. In a high frequency range where the transfer gain of diffraction of extracorporeal sounds is low, the coefficient of the adaptive filter is difficult to update, and the simulation accuracy of the diffracted component of the extracorporeal sounds in the intracorporeal sound signal is low. Therefore, as illustrated in FIG. 5 to FIG. 7, processing of the improved adaptive filter unit 4 is executed.

Figure 8:
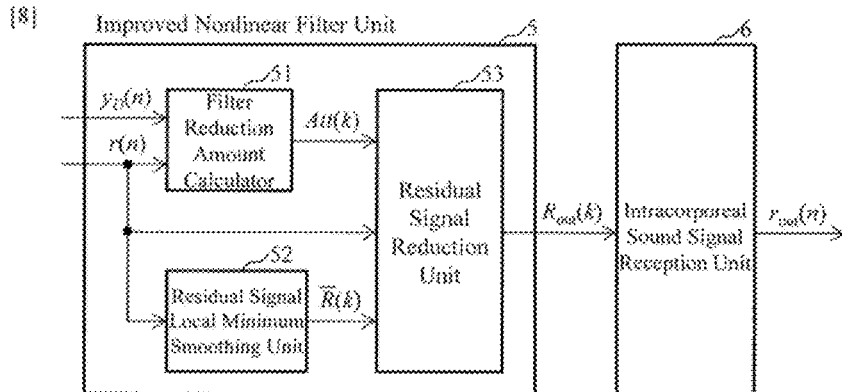
FIG. 8 is a diagram illustrating components of an improved nonlinear filter unit of the present disclosure.
Figure 9:
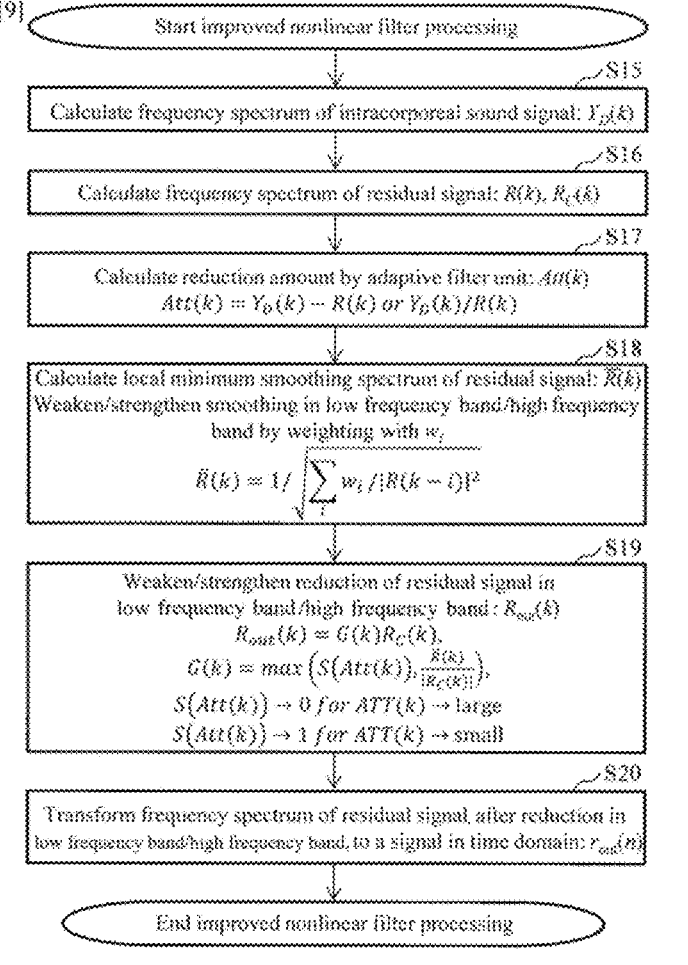
FIG. 9 is a diagram illustrating a processing procedure of the improved nonlinear filter unit of the present disclosure.
Figure 10:
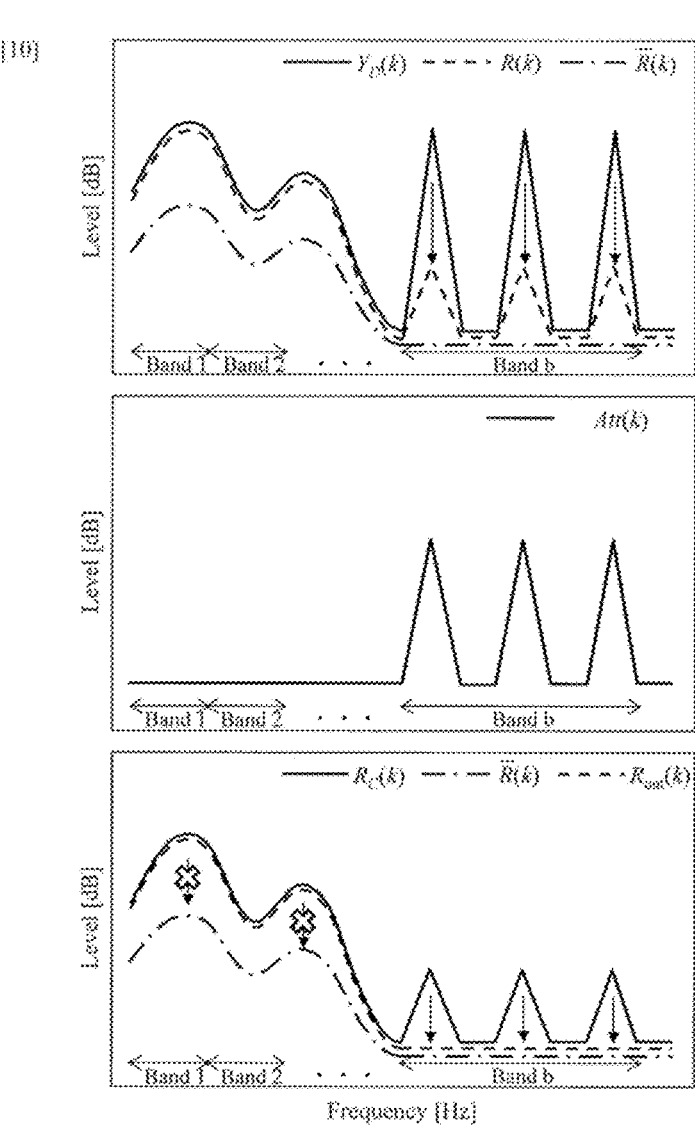
FIG. 10 is a diagram illustrating a processing concept of the improved nonlinear filter unit of the present disclosure.

FIG. 4 is a schematic diagram of reduction effects by a conventional nonlinear filter. In an upper row of FIG. 4, a reduction effect by the nonlinear filter that deepens troughs of a spectrum is illustrated. Then, the reduction effect from a residual signal to a reduction signal by the nonlinear filter is noise removal, as desired, in a low frequency range, but is unintentionally noise enhancement in a high frequency range. In a lower row of FIG. 4, a reduction effect by the nonlinear filter that crushes crests of a spectrum is illustrated. Then, the reduction effect from the residual signal to the reduction signal by the nonlinear filter is noise removal, as desired, in the high frequency range, but is unintentionally signal removal in the low frequency range. Therefore, as illustrated in FIG. 8 to FIG. 10, processing of the improved nonlinear filter unit 5 is executed.
(Processing Concept of Improved Adaptive Filter Unit of Present Disclosure)

Figure 5:
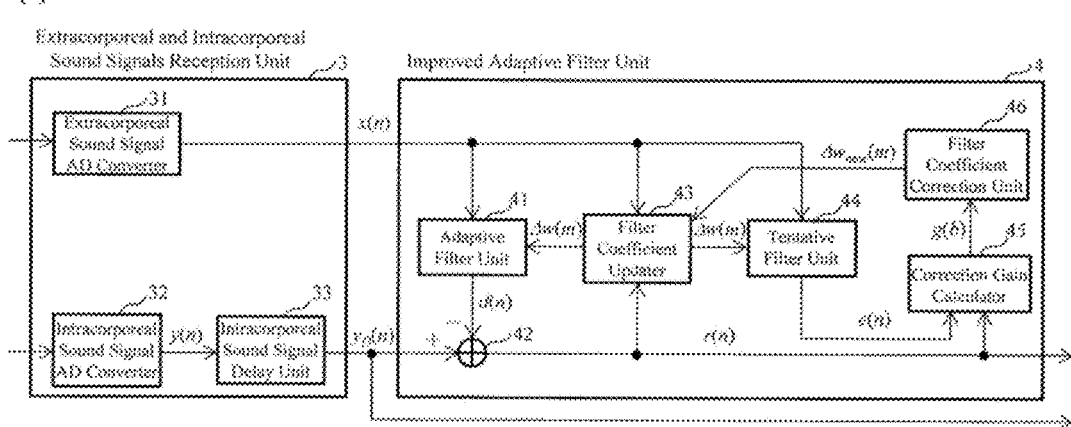
FIG. 5 is a diagram illustrating components of an improved adaptive filter unit of the present disclosure.

FIG. 5 illustrates components of an improved adaptive filter unit of the present disclosure. FIG. 6 illustrates a processing procedure of the improved adaptive filter unit of the present disclosure. FIG. 7 illustrates a processing concept of the improved adaptive filter unit of the present disclosure. The extracorporeal and intracorporeal sound signals reception unit 3 includes an extracorporeal sound signal AD converter 31, an intracorporeal sound signal AD converter 32, and an intracorporeal sound signal delay unit 33. The improved adaptive filter unit 4 includes an adaptive filter unit 41, a residual signal calculator 42, a filter coefficient updater 43, a tentative filter unit 44, a correction gain calculator 45, and a filter coefficient correction unit 46. The extracorporeal and intracorporeal sound signals reception unit 3 and the improved adaptive filter unit 4 can be achieved by installing an improved adaptive filter program, illustrated in FIG. 6, on a computer.

The extracorporeal sound signal AD converter 31 outputs an extracorporeal sound signal x(n) after AD conversion (Step S1). The intracorporeal sound signal AD converter 32 outputs an intracorporeal sound signal y(n) after AD conversion (Step S2). The intracorporeal sound signal delay unit 33 outputs an intracorporeal sound signal $y_D(n)=y(n-D)$ after a delay D of a constant time (Step S3).

The adaptive filter unit 41 has an adaptive filter coefficient, a current value of which is defined as w(m), simulating diffraction from the extracorporeal sound collector 1 to the intracorporeal sound collector 2, receives the extracorporeal sound signal x(n), and outputs an adaptive filter signal $d(n)=\Sigma w(m) \times (n-m)$ (the sum is calculated with m=0 to M) (Step S4). Here, M is an order of the adaptive filter unit 41. The adaptive filter unit 41 may execute processing in a frequency domain corresponding to processing in a time domain.

The residual signal calculator 42 subtracts the adaptive filter signal d(n) (a simulation signal of a diffracted component of the extracorporeal sound signal x(n)) from the intracorporeal sound signal $y_D(n)$ to calculate a residual signal $r(n)=y_D(n)-d(n)$ intended to be a result of taking the diffracted component of the extracorporeal sound signal x(n) from the intracorporeal sound signal $y_D(n)$ (Step S5).

The filter coefficient updater 43 adds an updater value $\Delta w(m)$ of the adaptive filter coefficient to the current value w(m) of the adaptive filter coefficient so as to lower a correlation in a time axis direction between the adaptive filter signal d(n) and the residual signal r(n) (Step S6, Math. 1). Here, µ and λ are fixed or time-variant control parameters and determine a magnitude of the updater value $\Delta w(m)$ of the adaptive filter coefficient.

$$w(m) \leftarrow w(m) + \Delta w(m), \Delta w(m) = \mu \frac{r(n)x(n-m)}{\sum_{m=0}^{M}|x(n-m)|^2 + \lambda} \qquad \text{(Math. 1)}$$

The tentative filter unit 44 has a tentative filter coefficient $\Delta w(m)$ chosen to be equal to the updater value $\Delta w(m)$ of the adaptive filter coefficient, receives the extracorporeal sound signal x(n), and outputs a tentative filter signal $e(n)=\Sigma \Delta w(m) \times (n-m)$ (the sum is calculated with m=0 to M) (Step S7). Here, M is an order of the tentative filter unit 44. The tentative filter unit 44 may execute processing in a frequency domain corresponding to processing in a time domain.

The correction gain calculator 45 calculates a correction gain g(b) for a frequency spectrum $\Delta W(k)$ of the updater value $\Delta w(m)$ of the adaptive filter coefficient, as a relatively large value, within a high frequency band b where a frequency-band-limited correlation between a frequency spectrum R(k) of the residual signal r(n) and a frequency spectrum E(k) of the tentative filter signal e(n) is high (Steps S8 to S10, high frequency bands in an upper row and a middle row of FIG. 7).

In contrast, the correction gain calculator 45 calculates the correction gain g(b) for the frequency spectrum $\Delta W(k)$ of the updater value $\Delta w(m)$ of the adaptive filter coefficient, as a relatively small value, within the low frequency band b where the frequency-band-limited correlation between the frequency spectrum R(k) of the residual signal r(n) and the frequency spectrum E(k) of the tentative filter signal e(n) is low (Steps S8 to S10, low frequency bands in the upper row and the middle row of FIG. 7).

Specifically, the correction gain calculator 45 calculates the correction gain g(b), for the frequency spectrum $\Delta W(k)$ of the updater value $\Delta w(m)$ of the adaptive filter coefficient, corresponding to each band b such that, based on the frequency-band-limited correlation between the frequency spectrum R(k) of the residual signal r(n) and the frequency spectrum E(k) of the tentative filter signal e(n) resulting from multiplication by the correction gain g(b), corresponding to each band b, a spectral-shape error corresponding to each band b of both frequency spectra R(k) and E(k) is minimized (Steps S8 to S10, the upper row and the middle row of FIG. 7: the correction gain g(b) in a b-th band of divided bands).

First, the spectrum R(k) for amplitude or power of the residual signal r(n) for a short time is calculated, and the spectra R(k) within the b-th band are vectorized together into R(b) (Step S8). Next, the spectrum E(k) for amplitude or power of the tentative filter signal e(n) for a short time is calculated, and the spectra E(k) within the b-th band are vectorized together into E(b) (Step S9). Next, the correction gain g(b) for the frequency spectrum $\Delta W(k)$ of the updater value $\Delta w(m)$ of the adaptive filter coefficient is calculated (Step S10, Math. 2). Here, < > is an inner product.

$$g(b) = \langle E(b), R(b) \rangle / \|E(b)\|^2 \text{ minimizing } \|R(b) - g(b)E(b)\|^2 \qquad \text{(Math. 2)}$$

The filter coefficient correction unit 46 calculates a correction value $\Delta w_{new}(m)$ relative to the updater value $\Delta w(m)$ of the adaptive filter coefficient based on the correction gain g(b) relative to the frequency spectrum $\Delta W(k)$ of the updater value $\Delta w(m)$ of the adaptive filter coefficient (Steps S11 to S14, a plurality of bands b in the upper row and the middle row of FIG. 7: high frequency bands and low frequency bands). Without applying the updater value $\Delta w(m)$ of the adaptive filter coefficient (Step S6), the filter coefficient updater 43 applies the correction value $\Delta w_{new}(m)$ relative to the updater value $\Delta w(m)$ of the adaptive filter coefficient (Step S14).

First, the frequency spectrum $\Delta W(k)$ of the updater value $\Delta w(m)$ of the adaptive filter coefficient is calculated (Step S11). Next, the frequency spectrum $\Delta W(k)$ of the updater value $\Delta w(m)$ of the adaptive filter coefficient is corrected to $\Delta W_{new}(k)=g(b)\Delta W(k)$ within the b-th band (Step S12). Next, a frequency spectrum $\Delta W_{new}(k)$ of the correction value $\Delta w_{new}(m)$ of the adaptive filter coefficient is transformed to $\Delta w_{new}(m)$ in a time domain (Step S13). Next, the updater value $\Delta w(m)$ of the adaptive filter coefficient is corrected to $\Delta w_{new}(m)$ (Step S14).

Figure 11:
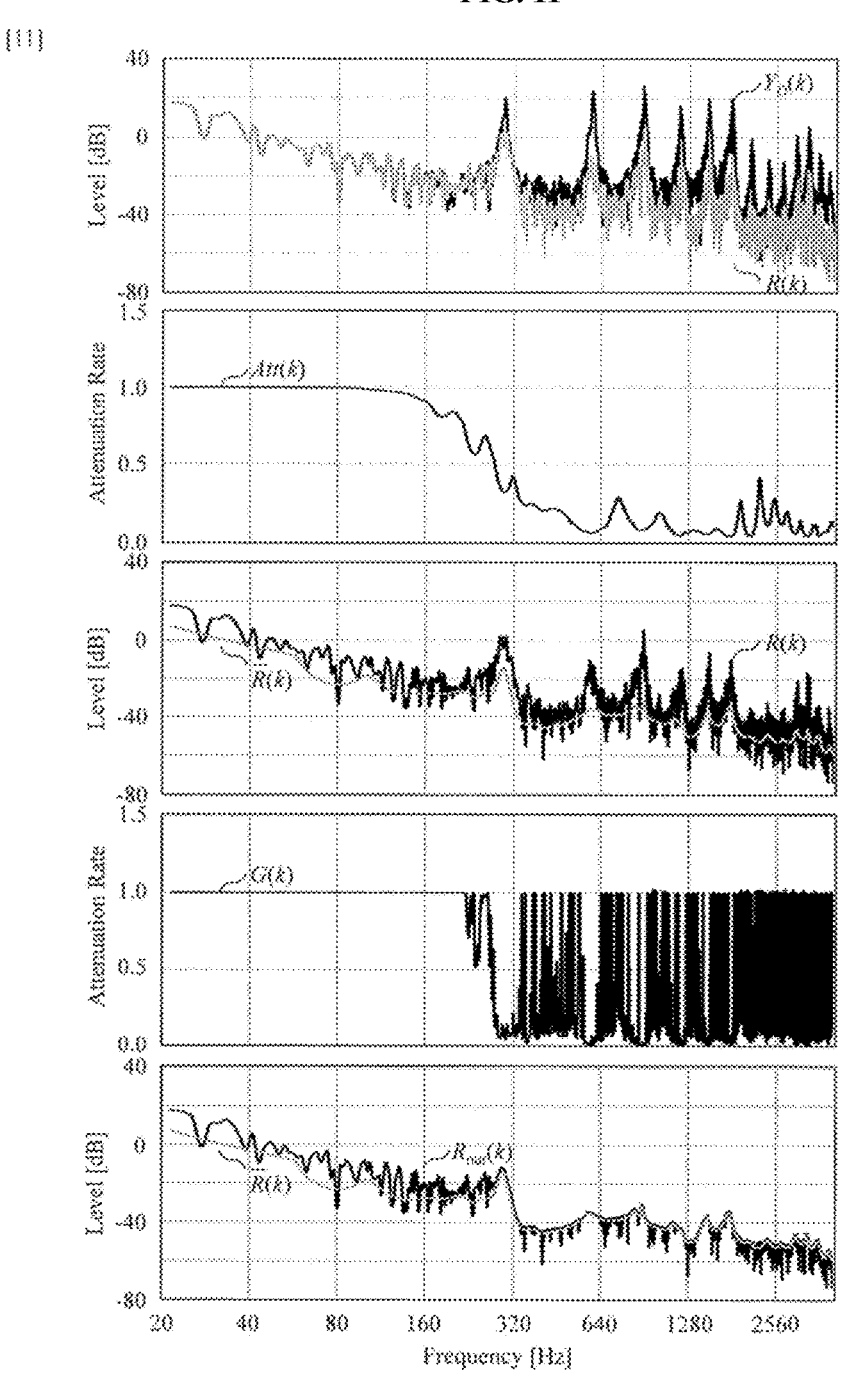
FIG. 11 is a diagram illustrating a processing result of an electronic stethoscope signal processor of the present disclosure.

Although, in a high frequency band in a lower row of FIG. 7, the frequency spectrum R(k) of the residual signal r(n) includes many diffracted components of extracorporeal sounds before the correction of the updater value $\Delta w(m)$ of the adaptive filter coefficient, the diffracted components of extracorporeal sounds are not always eliminated by the correction of the updater value $\Delta w(m)$ of the adaptive filter coefficient and reduced diffracted components of extracorporeal sounds are capable of being left after the correction (a first row of FIG. 11). In a low frequency bands in the lower row of FIG. 7, the frequency spectrum R(k) of the residual signal r(n) mainly includes components of intracorporeal sounds before the correction of the updater value $\Delta w(m)$ of the adaptive filter coefficient, and the components of intracorporeal sounds are nearly kept up before and after the correction of the updater value Δw(m) of the adaptive filter coefficient.

Accordingly, intracorporeal sounds (such as low-frequency-range heart sounds or breath sounds) can be extracted by not only reducing steady noise (such as low-frequency-range environmental sounds or noise), as has been achievable by the related art, but also reducing unexpected noise (such as high-frequency-range cries or speaking voices), as becomes achievable by the present disclosure. Then, a reduction level of the unexpected noise (such as high-frequency-range cries or speaking voices) and a level of keeping up the intracorporeal sounds (such as low-frequency-range heart sounds or breath sounds) can be quantitatively calculated.

(Processing Concept of Improved Nonlinear Filter Unit of Present Disclosure)

FIG. 8 illustrates components of an improved nonlinear filter unit of the present disclosure. FIG. 9 illustrates a processing procedure of the improved nonlinear filter unit of the present disclosure. FIG. 10 illustrates a processing concept of the improved nonlinear filter unit of the present disclosure. The improved nonlinear filter unit 5 includes a filter reduction amount calculator 51, a residual signal local minimum smoothing unit 52, and a residual signal reduction unit 53. The improved nonlinear filter unit 5 and the intracorporeal sound signal output unit 6 can be achieved by installing an improved nonlinear filter program, illustrated in FIG. 9, on a computer.

The filter reduction amount calculator 51 calculates a reduction amount of the frequency spectrum R(k) of the residual signal r(n), relative to a frequency spectrum $Y_D(k)$ of the intracorporeal sound signal $y_D(n)$, to calculate a reduction amount Att(k) by the improved adaptive filter unit 4 (including the filter coefficient correction unit 46) (Steps S15 to S17, a plurality of bands b at an upper row and a middle row of FIG. 10: high frequency bands and low frequency bands).

First, the spectrum $Y_D(k)$ for amplitude or power of the intracorporeal sound signal $y_D(n)$ for a short time is calculated (Step S15). Next, the spectrum R(k) for amplitude or power of the residual signal r(n) for a short time is calculated (Step S16). Next, the reduction amount Att(k)=$Y_D(k)$−R(k), $Y_D(k)$/R(k), or log($Y_D(k)$/R(k)) by the improved adaptive filter unit 4 is calculated (Step S17). Here, the reduction amount Att(k) by the improved adaptive filter unit 4 may be an average value in a predetermined bandwidth related to any of the reduction amounts in Step S17.

The residual signal local minimum smoothing unit 52 calculates a local minimum smoothing spectrum $\overline{R}$(k) of the residual signal r(n) so as to retain a local minimal value of the frequency spectrum R(k) of the residual signal r(n) (Step S18, a plurality of bands b at the upper row and a lower row of FIG. 10: high frequency bands and low frequency bands).

As one method, for the frequency spectrum R(k) of the residual signal r(n), a square root of an inverse of a mean square of an inverse in a predetermined bandwidth may be calculated as the local minimum smoothing spectrum $\overline{R}$(k) of the residual signal r(n) (Step S18, Math. 3). Here, $w_i$ is a weighting factor given for a frequency i within a predetermined band to weaken/strengthen smoothing in a low frequency band/high frequency band. As another method, for the frequency spectrum R(k) of the residual signal r(n), a search result of a minimum value in a predetermined bandwidth may be calculated as the local minimum smoothing spectrum $\overline{R}$(k) of the residual signal r(n) (Step S18).

$$\overline{R}(k) = 1 \left/ \sqrt{\sum_i w_i / |R(k-i)|^2} \right. \qquad \text{(Math. 3)}$$

The residual signal reduction unit 53 largely reduces a complex frequency spectrum $R_C(k)$ of the residual signal r(n) to a spectrum further approaching the local minimum smoothing spectrum $\overline{R}$(k) of the residual signal r(n), within a frequency band where the reduction amount Att(k) by the improved adaptive filter unit 4 is large, to calculate a reduction frequency spectrum $R_{out}(k)$ of the residual signal r(n) (Step S19, high frequency bands in a middle row and the lower row of FIG. 10).

The residual signal reduction unit 53 sparingly reduces the complex frequency spectrum $R_C(k)$ of the residual signal r(n) to a spectrum further approaching the local minimum smoothing spectrum $\overline{R}$(k) of the residual signal r(n), within frequency bands where the reduction amount Att(k) by the improved adaptive filter unit 4 is small, to calculate the reduction frequency spectrum $R_{out}(k)$ of the residual signal r(n) (Step S19, low frequency bands in the middle row and the lower row of FIG. 10).

The residual signal reduction unit 53 may retain the complex frequency spectrum $R_C(k)$ of the residual signal r(n) as the reduced frequency spectrum $R_{out}(k)$ of the residual signal r(n), without reducing it to a spectrum further approaching the local minimum smoothing spectrum $\overline{R}$(k) of the residual signal r(n), within frequency bands where the reduction amount Att(k) by the improved adaptive filter unit 4 is small (Step S19, the low frequency bands in the middle row and the lower row of FIG. 10).

Specifically, the reduction frequency spectrum $R_{out}(k)$ of the residual signal r(n) is calculated based on Math. 4. Here, G(k) is a correction gain from the complex frequency spectrum $R_C(k)$ of the residual signal r(n) to the reduction frequency spectrum $R_{out}(k)$ of the residual signal r(n). Then, S(Att(k)) approaches 0 as Att(k) becomes larger and approaches 1 as Att(k) becomes smaller. Furthermore, max (a, b) is a maximum value of the set of a and b.

$$R_{out}(k) = G(k)R_C(k), \ G(k) = \max\left(S(Att(k)), \frac{\overline{R}(k)}{|R_C(k)|}\right) \qquad \text{(Math. 4)}$$

Accordingly, a frequency band where the reduction amount Att(k) by the improved adaptive filter unit 4 is large results in, S(Att(k))→0, 0<$\overline{R}$(k)/|$R_C(k)$|<1, G(k)=$\overline{R}$(k)/|$R_C(k)$|, and $R_{out}(k)$=$R_C(k)$*$\overline{R}$(k)/|$R_C(k)$|. On the other hand, a frequency band where the reduction amount Att(k) by the improved adaptive filter unit 4 is small results in, S(Att(k))→1, 0<$\overline{R}$(k)/|$R_C(k)$|<1, G(k)→1, and $R_{out}(k)$ →$R_C(k)$.

The intracorporeal sound signal output unit 6 transforms the reduction frequency spectrum $R_{out}(k)$ of the residual signal r(n) to a reduction signal $r_{out}(n)$ of the residual signal r(n) in the time domain (Step S20).

Accordingly, intracorporeal sounds (such as low-frequency-range heart sounds or breath sounds) can be extracted by not only reducing steady noise (such as low-frequency-range environmental sounds or noise), as has been achievable by the related art, but also reducing unexpected noise (such as high-frequency-range cries or speaking voices), as becomes achievable by the present disclosure. Then, the reduction level of the unexpected noise (such as high-frequency-range cries or speaking voices) and the level of keeping up the intracorporeal sounds (such as low-frequency-range heart sounds or breath sounds) can be quantitatively calculated.

(Processing Result of Electronic Stethoscope Signal Processor of Present Disclosure)

FIG. 11 illustrates a processing result of an electronic stethoscope signal processor of the present disclosure. In a first row of FIG. 11, the frequency spectrum R(k) of the residual signal r(n) is kept up in a low frequency range and reduced in a high frequency range, compared with the frequency spectrum $Y_D$(k) of the intracorporeal sound signal $y_D$(n). In a second row of FIG. 11, the reduction amount Att(k) by the improved adaptive filter unit 4 is small (attenuation rate=after attenuation/before attenuation→1) in a low frequency range and large (attenuation rate=after attenuation/before attenuation→0) in a high frequency range.

In a third row of FIG. 11, the local minimum smoothing spectrum R⁻(k) of the residual signal r(n) is positioned over local minimal values of the frequency spectrum R(k) of the residual signal r(n) in a low frequency range and is also positioned over local minimal values in a high frequency range. In a fourth row of FIG. 11, the correction gain G(k) to the complex frequency spectrum $R_C$(k) of the residual signal r(n) approaches 1 (attenuation rate=after attenuation/before attenuation→1) in troughs in a low frequency range and a high frequency range, and approaches 0 (attenuation rate=after attenuation/before attenuation→0) in crests in the high frequency range.

In a fifth row of FIG. 11, the reduction frequency spectrum $R_{out}$(k) of the residual signal r(n) is not reduced in a low frequency range and is reduced to a spectrum further approaching the local minimum smoothing spectrum R⁻(k) of the residual signal r(n) in a high frequency range, compared with the frequency spectrum R(k) of the residual signal r(n).

Figure 12:
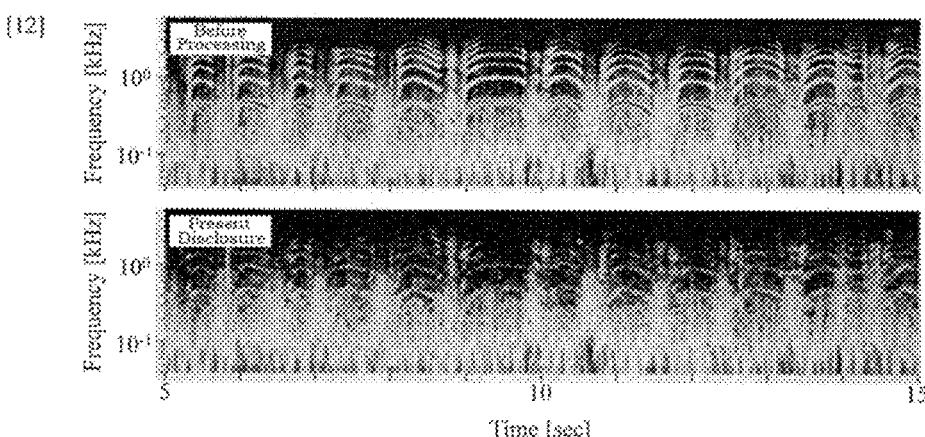
FIG. 12 is a diagram illustrating processing results of electronic stethoscope signal processors of the related art and the present disclosure.

FIG. 12 illustrates processing results of electronic stethoscope signal processors of the related art and the present disclosure. In a first row of FIG. 12, a spectrum of an intracorporeal sound signal before the processing of the present disclosure is illustrated, and a spectrum of a cry, which is a diffracted component of unexpected extracorporeal sounds in a band of 1 kHz or higher, is clearly illustrated. In a second row of FIG. 12, a spectrum of an intracorporeal sound signal after the processing of the present disclosure is illustrated, and a spectrum of a cry, which is a diffracted component of unexpected extracorporeal sounds in a band of 1 kHz or higher, is almost reduced.

In the embodiment, after the processing by the improved adaptive filter unit 4 (including the filter coefficient correction unit 46) is executed, the processing by the improved nonlinear filter unit 5 is executed. As a first modification, only the processing by the improved adaptive filter unit 4 (including the filter coefficient correction unit 46) may be executed. As a second modification, after the processing by the adaptive filter unit 41 (not including the filter coefficient correction unit 46) is executed, the processing by the improved nonlinear filter unit 5 may be executed.

INDUSTRIAL APPLICABILITY

The electronic stethoscope signal processor, the electronic stethoscope system, the electronic stethoscope signal processing program, and the electronic stethoscope signal processing method of the present disclosure (1) allow for medical examination, without depending on empirical knowledge, by converting intracorporeal sound signals into data, (2) allow for a response out of medical examination hours by recording the intracorporeal sound signals, and (3) allow for remote medical examination by communicating the intracorporeal sound signals.

DESCRIPTION OF REFERENCE NUMERALS

S: Electronic stethoscope system
E: Electronic stethoscope
P: Electronic stethoscope signal processor
B: Body surface
1: Extracorporeal sound collector
2: Intracorporeal sound collector
3: Extracorporeal and intracorporeal sound signals reception unit
4: Improved adaptive filter unit
5: Improved nonlinear filter unit
6: Intracorporeal sound signal output unit
31: Extracorporeal sound signal AD converter
32: Intracorporeal sound signal AD converter
33: Intracorporeal sound signal delay unit
41: Adaptive filter unit
42: Residual signal calculator
43: Filter coefficient updater
44: Tentative filter unit
45: Correction gain calculator
46: Filter coefficient correction unit
51: Filter reduction amount calculator
52: Residual signal local minimum smoothing unit
53: Residual signal reduction unit

What is claimed is:

1. An electronic stethoscope signal processor comprising:
an adaptive filter unit, wherein an adaptive filter is modified by an adaptive filter program loaded on a computer, wherein said modified adaptive filter has adaptive filter coefficients simulating a diffraction property of an extracorporeal sound from an outside of an electronic stethoscope to an intracorporeal sound collector, receives an extracorporeal sound signal obtained from an extracorporeal sound collector, and outputs an adaptive filter signal;
a residual signal calculator that subtracts the adaptive filter signal from an intracorporeal sound signal, obtained from the intracorporeal sound collector, to calculate a residual signal intended to be a result of taking a diffracted component of the extracorporeal sound signal from the intracorporeal sound signal;
a filter coefficient updater that adds updater values of the adaptive filter coefficients to current values of the adaptive filter coefficients so as to lower a correlation in a time axis direction between the adaptive filter signal and the residual signal;
a tentative filter unit, wherein a tentative filter is modified by a tentative filter program loaded on the computer, wherein said modified tentative filter has tentative filter coefficients chosen to be equal to the updater values of the adaptive filter coefficients, receives the extracorporeal sound signal, and outputs a tentative filter signal;
a correction gain calculator that calculates larger correction gains for a frequency spectrum of the updater values of the adaptive filter coefficients, within frequency bands where a frequency-band-limited correlation between a frequency spectrum of the residual signal and a frequency spectrum of the tentative filter signal is higher, and calculates smaller correction gains for the frequency spectrum of the updater values of the adaptive filter coefficients, within frequency bands where the frequency-band-limited correlation between the frequency spectrum of the residual signal and the frequency spectrum of the tentative filter signal is lower; and a filter coefficient correction unit, wherein a filter coefficient correction is modified by a filter coefficient correction program loaded on the computer, wherein said modified filter coefficient correction calculates a correction value, relative to the updater values of the adaptive filter coefficients based on the correction gains relative to the frequency spectrum of the updater values of the adaptive filter coefficients.

2. The electronic stethoscope signal processor according to claim 1, wherein the correction gain calculator calculates the correction gains for the frequency spectrum of the updater values of the adaptive filter coefficients, corresponding to each band such that, based on a frequency-band-limited correlation between the frequency spectrum of the residual signal and the frequency spectrum of the tentative filter signal resulting from multiplication by the correction gains, corresponding to each band, a spectral-shape error between the residual signal and the tentative filter signal resulting from the multiplication is minimized.

3. The electronic stethoscope signal processor according to claim 1, further comprising:

a filter reduction amount calculator that calculates a reduction amount of the frequency spectrum of the residual signal, relative to a frequency spectrum of the intracorporeal sound signal, to calculate a reduction amount by the adaptive filter unit; and a residual signal reduction unit, wherein a residual signal reduction is modified by a residual signal reduction program loaded on the computer, wherein said modified residual signal reduction more largely reduces the frequency spectrum of the residual signal within frequency bands where the reduction amount by the adaptive filter unit is larger, and retains or more sparingly reduces the frequency spectrum of the residual signal within frequency bands where the reduction amount by the adaptive filter unit is smaller.

4. The electronic stethoscope signal processor according to claim 3, further comprising a residual signal local minimum smoothing unit, wherein a residual signal local minimum smoothing is modified by a residual signal local minimum smoothing program loaded on the computer, wherein said modified residual signal local minimum smoothing calculates a local minimum smoothing spectrum of the residual signal so as to retain a local minimal value of the frequency spectrum of the residual signal, wherein the residual signal reduction unit more largely reduces the frequency spectrum of the residual signal, to a spectrum further approaching the local minimum smoothing spectrum of the residual signal, within the frequency bands where the reduction amount by the adaptive filter unit is larger, and retains the frequency spectrum of the residual signal or more sparingly reduces the frequency spectrum of the residual signal, to a spectrum approaching the local minimum smoothing spectrum of the residual signal, within the frequency bands where the reduction amount by the adaptive filter unit is smaller.

5. An electronic stethoscope system comprising:

the electronic stethoscope signal processor according to claim 1;

the extracorporeal sound collector that collects an extracorporeal sound and outputs the extracorporeal sound signal; and the intracorporeal sound collector that collects an intracorporeal sound and outputs the intracorporeal sound signal.

6. An electronic stethoscope signal processing program product for instructing the computer to execute each processing step by each component unit of the electronic stethoscope signal processor according to claim 1.

7. An electronic stethoscope signal processing method comprising each processing step by each component unit modified by an electronic stethoscope signal processing program loaded on the computer of the electronic stethoscope signal processor according to claim 1.

8. An electronic stethoscope signal processor comprising:

an adaptive filter unit, wherein an adaptive filter is modified by an adaptive filter program loaded on a computer, wherein said modified adaptive filter has adaptive filter coefficients simulating a diffraction property of an extracorporeal sound from an outside of an electronic stethoscope to an intracorporeal sound collector, receives an extracorporeal sound signal obtained from an extracorporeal sound collector, and outputs an adaptive filter signal;

a residual signal calculator that subtracts the adaptive filter signal from an intracorporeal sound signal, obtained from the intracorporeal sound collector, to calculate a residual signal intended to be a result of taking a diffracted component of the extracorporeal sound signal from the intracorporeal sound signal;

a filter coefficient updater that adds updater values of the adaptive filter coefficients to current values of the adaptive filter coefficients so as to lower a correlation in a time axis direction between the adaptive filter signal and the residual signal;

a filter reduction amount calculator that calculates a reduction amount of a frequency spectrum of the residual signal, relative to a frequency spectrum of the intracorporeal sound signal, to calculate a reduction amount by the adaptive filter unit; and a residual signal reduction unit, wherein a residual signal reduction is modified by a residual signal reduction program loaded on the computer, wherein said modified residual signal reduction more largely reduces the frequency spectrum of the residual signal within frequency bands where the reduction amount by the adaptive filter unit is larger, and retains or more sparingly reduces the frequency spectrum of the residual signal within frequency bands where the reduction amount by the adaptive filter unit is smaller.

9. The electronic stethoscope signal processor according to claim 8, further comprising a residual signal local minimum smoothing unit, wherein a residual signal local minimum smoothing is modified by a residual signal local minimum smoothing program loaded on the computer, wherein said modified residual signal local minimum smoothing calculates a local minimum smoothing spectrum of the residual signal so as to retain a local minimal value of the frequency spectrum of the residual signal, wherein the residual signal reduction unit more largely reduces the frequency spectrum of the residual signal, to a spectrum further approaching the local minimum smoothing spectrum of the residual signal, within frequency bands where the reduction amount by the adaptive filter unit is larger, and retains the frequency spectrum of the residual signal or more sparingly reduces the frequency spectrum of the residual signal, to a spectrum approaching the local minimum smoothing spectrum of the residual signal, within frequency bands where the reduction amount by the adaptive filter unit is smaller.

10. An electronic stethoscope system comprising:

the electronic stethoscope signal processor according to claim 8;

the extracorporeal sound collector that collects an extracorporeal sound and outputs the extracorporeal sound signal; and the intracorporeal sound collector that collects an intracorporeal sound and outputs the intracorporeal sound signal.

11. An electronic stethoscope signal processing program product for instructing the computer to execute each processing step by each component unit of the electronic stethoscope signal processor according to claim 8.

12. An electronic stethoscope signal processing method comprising each processing step by each component unit modified by an electronic stethoscope signal processing program loaded on the computer of the electronic stethoscope signal processor according to claim 8.

\* \* \* \* \*